United States Patent
Park et al.

(10) Patent No.: US 10,934,171 B2
(45) Date of Patent: Mar. 2, 2021

(54) FUNCTIONALIZED GRAPHENE COMPRISING TWO OR MORE TYPES OF AMINES, AND PREPARATION METHOD THEREFOR

(71) Applicant: Dongjin Semichem Co., Ltd., Incheon (KR)

(72) Inventors: Sunchan Park, Gyeonggi-do (KR); Hyeonseong Choe, Gyeonggi-do (KR); Soo Yeon Lee, Gyeonggi-do (KR); Seon Yeong Gong, Gyeonggi-do (KR)

(73) Assignee: Dongjin Semichem Co., Ltd., Incheon (KR)

( * ) Notice: Subject to any disclaimer, the term of this patent is extended or adjusted under 35 U.S.C. 154(b) by 499 days.

(21) Appl. No.: 15/822,795

(22) Filed: Nov. 27, 2017

(65) Prior Publication Data

US 2018/0079647 A1    Mar. 22, 2018

Related U.S. Application Data

(63) Continuation of application No. PCT/KR2016/005701, filed on May 30, 2016.

(30) Foreign Application Priority Data

May 28, 2015    (KR) .......................... 10-2015-0074793

(51) Int. Cl.
| | |
|---|---|
| *C01B 32/194* | (2017.01) |
| *C07C 211/51* | (2006.01) |
| *C07C 211/18* | (2006.01) |
| *C08K 3/04* | (2006.01) |
| *C01B 32/198* | (2017.01) |

(Continued)

(52) U.S. Cl.
CPC .......... *C01B 32/194* (2017.08); *C01B 32/198* (2017.08); *C07C 211/03* (2013.01);

(Continued)

(58) Field of Classification Search
CPC ............. C01B 32/194; C01B 2204/00; C01B 2204/02; C01B 2204/04; C01B 2204/06;

(Continued)

(56) References Cited

U.S. PATENT DOCUMENTS

| | | |
|---|---|---|
| 8,999,529 B2 | 4/2015 | Tetsuka et al. |
| 9,085,715 B2 | 7/2015 | Berthelot et al. |

(Continued)

FOREIGN PATENT DOCUMENTS

| | | |
|---|---|---|
| CN | 103466610 A | 12/2013 |
| JP | 2013-0006732 A | 1/2013 |

(Continued)

OTHER PUBLICATIONS

Li et al., "Simultaneous surface functionalization and reduction of graphene oxide with octadecylamine for electrically conductive polystyrene composites", Caron 49 (2011), pp. 4724-4730.

(Continued)

*Primary Examiner* — Daniel C. McCracken
(74) *Attorney, Agent, or Firm* — Nelson, Mullins, Riley & Scarborough LLP; Kongsik Kim, Esq.

(57) ABSTRACT

Disclosed is a functionalized graphene containing two or more amines having excellent electrical, thermal and mechanical properties by allowing good interfacial bonding force and uniform dispersion with a thermoplastic polymer, and a method for preparing the functional graphene. The functionalized graphene comprises a carbon material selected from the group consisting of graphene, reduced graphene, graphene oxide, and mixture thereof; and a monovalent amine group and a bivalent or higher amine group which are bonded to the carbon material.

15 Claims, 5 Drawing Sheets

(51) Int. Cl.
*C07C 211/03* (2006.01)
*C07C 211/09* (2006.01)

(52) U.S. Cl.
CPC .......... *C07C 211/09* (2013.01); *C07C 211/18* (2013.01); *C07C 211/51* (2013.01); *C08K 3/042* (2017.05); *C01B 2204/30* (2013.01); *C07C 2601/14* (2017.05); *C08J 2300/22* (2013.01); *C08J 2300/24* (2013.01); *C08K 2201/001* (2013.01)

(58) Field of Classification Search
CPC .......... C01B 2204/065; C01B 2204/20; C01B 2204/22; C01B 2204/24; C01B 2204/26; C01B 2204/28; C01B 2204/30; C01B 2204/32; C01B 32/20; C01B 32/205; C01B 32/21; C01B 32/215; C01B 32/22; C01B 32/225; C01B 32/23; C01B 32/198; C01B 32/182; C07C 211/18; C07C 211/51; C07C 211/09; C07C 211/03; C07C 2601/14; C08K 3/042; C08K 2201/001; C08J 2300/24; C08J 2300/22; C01P 2006/22
See application file for complete search history.

(56) References Cited

U.S. PATENT DOCUMENTS

| 2011/0159372 | A1* | 6/2011 | Zhamu | H01G 11/38 429/232 |
| 2012/0065309 | A1* | 3/2012 | Agrawal | B82Y 30/00 524/155 |
| 2013/0181165 | A1* | 7/2013 | Tetsuka | C09K 11/06 252/301.16 |

FOREIGN PATENT DOCUMENTS

| KR | 10-2010-0130999 | 12/2010 |
| KR | 10-2013-0134446 | 12/2013 |

OTHER PUBLICATIONS

Ma et al., "Functionalization and Reduction of Graphene Oxide with r-Phenylene Diamine for Electrically Conductive and Thermally Stable Polystyrene Composites", ACS Applied Materials & Interfaces, vol. 4, pp. 1998-1953 (2012).

* cited by examiner

FUNCTIONALIZED GRAPHENE COMPRISING TWO OR MORE TYPES OF AMINES, AND PREPARATION METHOD THEREFOR

CROSS-REFERENCE TO RELATED APPLICATIONS

This application is a continuation application of International Application No. PCT/KR2016/005701 filed on May 30, 2016, which claims priority to Korean Application No. 10-2015-0074793 filed on May 28, 2015. The applications are incorporated herein by reference.

TECHNICAL FIELD

The present invention relates functionalized graphene comprising two or more amines and method for preparing the same, and more particularly functionalized graphene comprising two or more amines which has good interfacial bonding force with thermoplastic polymers to uniformly disperse thermoplastic polymers so that electrical, thermal and mechanical properties thereof come to excellent and method for preparing the same.

BACKGROUND ART

A common pencil lead in everyday life is made of inexpensive graphite. The graphite is formed from carbon crystals of two-dimensional sheets, each stacked one above the other, atoms in each sheet being connected to a hexagonal, honeycomb-like shape. One layer constituting the graphite is called a graphene. The graphene is a material having both properties of metals and non-metals. Graphene is 311 times stronger than steel in tensile strength, 1,000 times faster than silicon in electron mobility and 10 times better than copper in thermal conductivity. Graphene is transparent enough to pass 98% of light and has the property that its characteristics are retained even when being bent or stretched. Owing to these properties, graphene can be applied in various fields such as nano materials, Inks, barrier materials, heat dissipation materials, ultra-light materials, energy electrode materials, next-generation semiconductors, transparent electrodes, etc.

The graphene may be a reduced graphene oxide (RGO) which is produced by acid-treating the graphite to produce a graphene oxide (GO) and then reducing the graphene oxide (GO). Recently, there is a trend to develop a functionalized graphene by using the graphene oxide and various functional agents having one amine at the terminal thereof.

Conventionally, a functionalized graphene can be represented by the structural formula 1 shown in FIG. 2, which is prepared by using monovalent amine (mono-amine) alone, or the bivalent amine (diamine) alone.

When the functionalized graphene is prepared by using monovalent amine alone, as can be seen from the reaction scheme 1 shown in FIG. 3, an amine functional group is not bonded to the surface of the graphene due to the reaction of the amine group with functional groups being on the surface of the graphene oxide, and there occurs alkylation thereby forming carbon chains such as linear, cyclic, and aromatic on the surface of the graphene. The introduction of amine makes application to hydrophobic solvents or polymer resins be difficult. That is, this method has limited applications.

Further when the functionalized graphene is prepared by using bivalent amine, for example, ethylenediamine (EDA) alone, there are some difficulties such that the process steps are increased due to the inevitable use of the catalyst and the need for pre-treatment of graphene oxide, the production cost is high resulted from using the catalyst, and agglomerates are occurred through a reduction process using a reducing agent because of the reduction process being performed after graphene oxide is functionalized.

Functionalized graphene using one amine alone is known ((Polymer (Korea), Vol. 35, No. 3, pp 265-271, 2011) (J. Mater. Chem. A, 2013,) (Korean Patent Application No. 10-2010-7016175). However, the known functionalized graphene has poor kneadability and dispersibility with various solvents and resins, so there is a problem that a specific solvent and a specific resin must be used.

Therefore, even when applied to various solvents and resins, graphene having excellent dispersibility and kneadability is required.

SUMMARY

Therefore, it is an object of the present invention to provide a functionalized graphene having two or more kinds of amine and having both hydrophilic and hydrophobic properties for good kneadability and dispersibility for various solvents and resins.

In order to achieve these objects, the present invention provides a functionalized graphene with amine groups comprising: a carbon material selected from a group consisting of graphene, reduced graphene, graphene oxide and mixture thereof; and a monovalent amine group and a bivalent or higher amine group which are bonded to the carbon material.

Further, the present invention provides a method for preparing a functionalized graphene comprising the steps of: mixing a carbon material and a first solvent to prepare a carbon material dispersion, the carbon material being selected from a group consisting of graphene, reduced graphene, graphene oxide and mixture thereof; and adding to the carbon material dispersion an amine solution in which a first amine compound having a monovalent amine group, a second amine compound having a bivalent or higher amine group and a second solvent are mixed to chemically bond the amine group to the carbon material.

Two or more amines have been applied to a functionalized graphene according to the present invention so that the functionalized graphene has hydrophilicity and hydrophobicity and as a result it has excellent kneadability with various solvents and resins.

DETAILED DESCRIPTION

Figure 1:
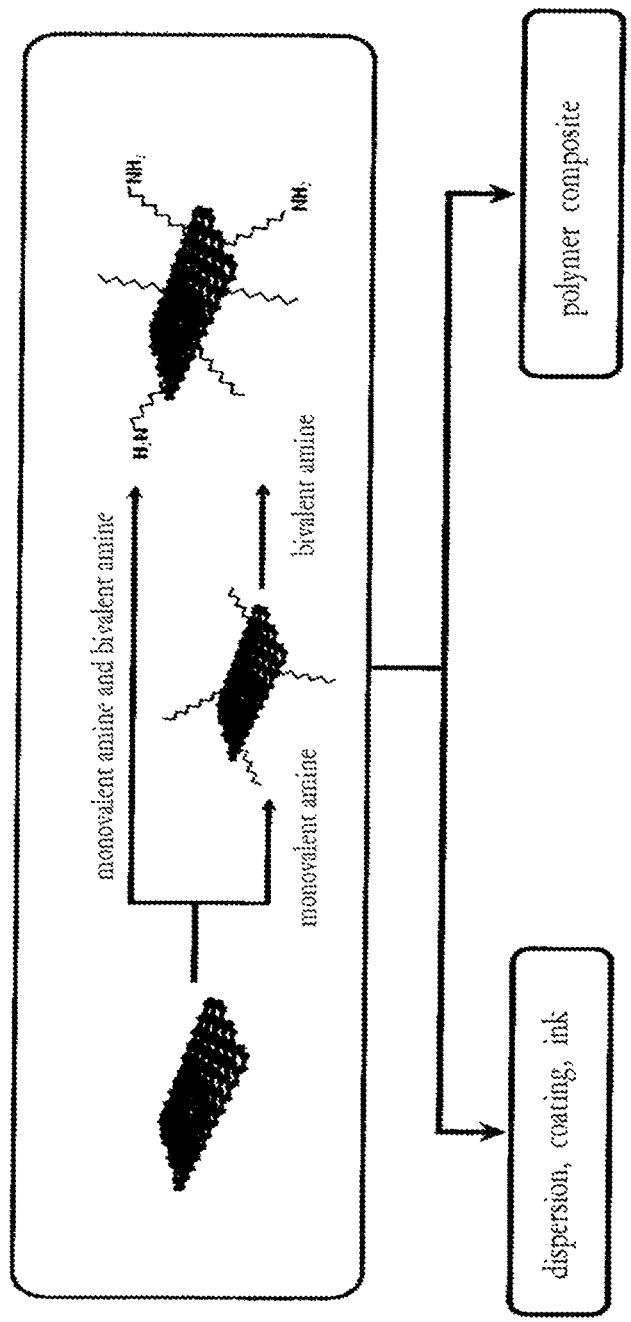
FIG. 1 is a drawing illustrating a preparation example (a) of a functionalized graphene according to the present invention and productions (b, c) using the same.
Figure 2:
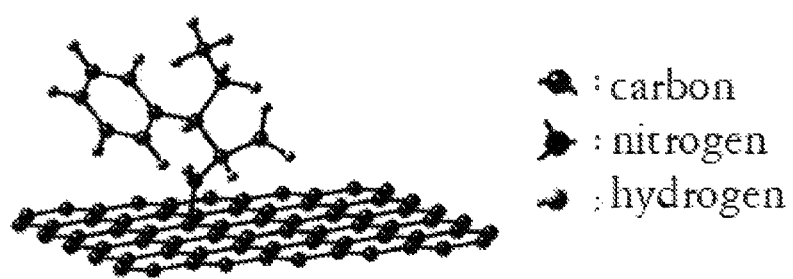
FIG. 2 shows the structural formula of a conventional functionalized graphene.
Figure 3:
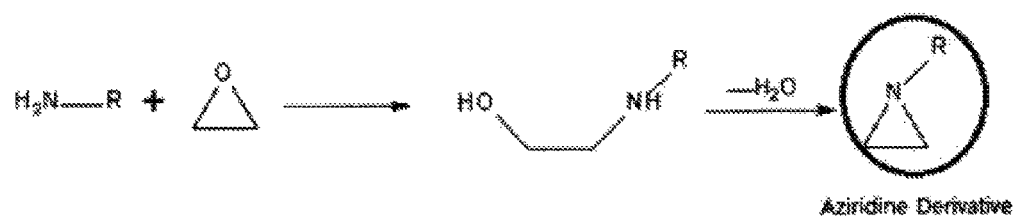
FIG. 3 shows a reaction scheme to prepare a conventional functionalized graphene.

Hereinafter, the present invention will be described in more detail with reference to the accompanying drawings.

The functionalized graphene according to the present invention has amphiphilic properties, that is, hydrophilic and hydrophobic, and thus has excellent kneadability with various solvents and resins. The functionalized graphene also includes carbon materials and amine groups.

The carbon material is excellent in electrical conductivity, thermal conductivity, dispersibility and compatibility, and is selected from a group of graphene, reduced graphene oxide (rGO), graphene oxide (GO), mixtures thereof, and the like.

The amine group is chemically bonded to the carbon material to improve the interfacial bonding strength with the thermoplastic polymer resin, thereby inducing uniform dispersion of the thermoplastic polymer resin so that it improves the electrical, thermal and mechanical properties of carbon materials. The amine group includes a monovalent amine (mono-amine) group and a bivalent or higher amine (di- or higher amine) group. Specifically, the monovalent amine group and the bivalent or higher amine group are bonded to different position of the carbon material.

The monovalent amine group may have one amine group and 1 to 40 carbon atoms, more specifically 2 to 25 carbon atoms, and most specifically 3 to 18 carbon atoms. For example, the monovalent amine group is an aliphatic monovalent amine group having 1 to 40 carbon atoms, specifically 2 to 25 carbon atoms, more specifically 3 to 18 carbon atoms. For example, the monovalent amine group may be a monovalent amine group selected from the group consisting of chain alkylamine group having 3 to 18 carbon atoms, a cyclic or aromatic alkylamine group having 6 to 15 carbon atoms. More specifically, the monovalent amine group is a chain alkylamine group having 3 to 18 carbon atoms. Examples include

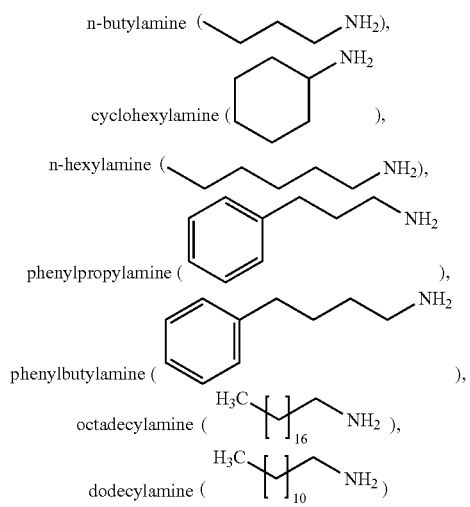

and so on. In the above-exemplified amine compounds, one hydrogen atom of the amine compound is substituted to form the monovalent amine group. The monovalent amine group has only one amine group in a molecule, and the only one amine group is chemically bonded to the carbon material.

The bivalent or higher amine group includes 2 or more amine groups, specifically 2 to 4 amine groups. For example, the bivalent or higher amine group may have 2 or more amine groups and 1 to 40 carbon atoms, more specifically 2 to 25 carbon atoms, and most specifically 3 to 15 carbon atoms. For example, the bivalent or higher amine group is an aliphatic bivalent or higher amine group having 1 to 40 carbon atoms, more specifically 2 to 25 carbon atoms, and most specifically 3 to 15 carbon atoms. Specifically, the bivalent or higher amine group may be selected from the group consisting of chain alkylamine group having 3 to 15 carbon atoms, a cyclic or aromatic alkylamine group having 6 to 15 carbon atoms. More specifically, the bivalent or higher amine group is a cyclic alkylamine group having 6 to 15 carbon atoms. Examples includes

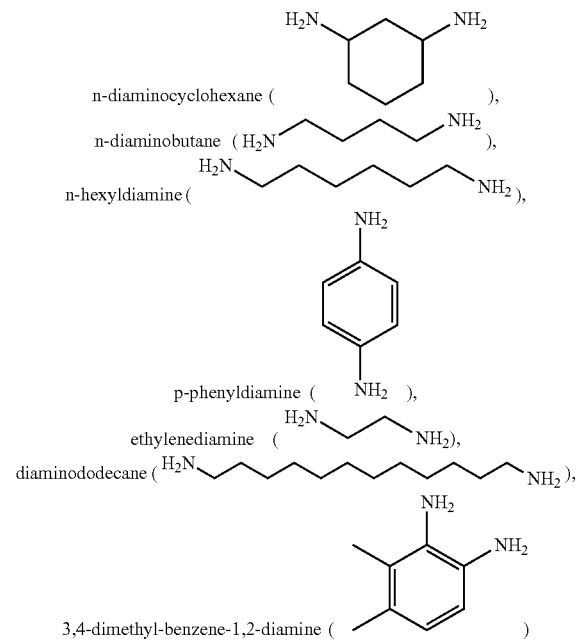

and so on. In the above-exemplified amine compounds, one hydrogen atom of the amine compound is substituted to form the bivalent or higher amine group. The bivalent or higher amine group has two or more amine groups in a molecule, and one amine group is chemically bonded to the carbon material, and other amine group(s) is not chemically bonded to the carbon material.

The molar ratio of the monovalent amine group and the bivalent or higher amine group which are bonded to the carbon material is 1:9 to 9:1, specifically 1:4 to 4:1. If the molar ratio of the monovalent amine group is too high, the distribution of the hydrophobic alkyl chains on the surface of functionalized graphene increases to weaken the interfacial bonding force with the hydrophilic solvent, thereby making it difficult to uniformly be dispersed in the solvent. If molar ratio of the bivalent or higher amine group is too high, a reaction of the bivalent amines before the functionalization of the graphene produces a side reaction (impurity) to degrade the electrical characteristics, or the bonding between amine groups present in the functionalized graphene causes formation of large aggregates to lower the dispersibility. In addition, since monovalent amine groups and bivalent or higher amine groups are bonded to the carbon material at different positions, the present invention can be applied regardless of the wide polarity of the solvent.

The amount the carbon material may be 85 to 99.9 wt (weight) %, specifically 90 to 99.9 wt %, and the amount of the amine group bonded to the carbon material may be 0.1 to 15 wt %, specifically 0.1 to 10 wt %. In terms of the amount of carbon and nitrogen components, with respect to the entire functionalized graphene, the amount of carbon component is 85 to 99.9 wt %, specifically 90 to 99.9 wt %, and the amount of nitrogen component is 0.1 to 15 wt %, specifically 0.1 to 10 wt %. If the amount of the carbon material is too small, characteristics of graphene may not be imparted, and if the amount of the carbon material is too large, dispersibility and kneadability may not be good. If the amount of the amine group is too low, aggregation can be caused due to the lowering of the dispersibility of the functionalized graphene, which may cause deterioration of the performance of the coating solution. If the amount of the amine group is too high, the hydrophilicity of the functionalized graphene is increased, and it is difficult to uniformly be dispersed in the hydrophobic solvent. Here, the kneadability means that the flow of the thermoplastic polymer resin melted at the elevated temperature is increased by the shearing force, and at the same time, the filler and the polymer resin are mixed to uniformly be dispersed in the thermoplastic polymer resin.

If necessary, the functionalized graphene according to the present invention can control hydrophilicity and hydrophobicity by controlling the molar ratio of amine groups chemically bonded to the carbon material. For example, in the above monovalent amine group and bivalent or higher amine group, when the molar ratio of the monovalent amine group is high, specifically, when the molar ratio of the monovalent group to the bivalent or higher amine group is from 6:4 to 9:1, more specifically from 7:3 to 9:1, hydrophobicity can be increased. Conversely, among the above monovalent amine groups and bivalent or higher valent amine groups, when the molar ratio of the bivalent or higher amine groups is high, specifically, when the molar ratio is of from 4:6 to 1:9, more specifically from 3:7 to 1:9, the hydrophilicity can be increased.

The functionalized graphene according to the present invention may further contain impurities generated in the manufacturing process in addition to carbon materials and amine groups. The impurities may be, for example, unreduced oxygen (O) in graphene oxide or the oxygen (O) in the defect of the manufacturing process of graphene oxide and in the atmosphere, or carboxyl group (—COOH), hydroxyl group (—OH), oxygen ($O_2$), and mixtures thereof, which may be caused by the influence of gas upon reaction in the atmosphere and errors in analysis.

When the impurity is contained, the amount of the carbon material (or amount of carbon component) in the functionalized graphene according to the present invention may be 74.9 to 97.89 wt %, specifically 81.7 to 97.7 wt %, the amount of the amine group (or amount of nitrogen component) may be 0.1 to 15 wt %, specifically 0.1 to 10 wt %, and the amount of the oxygen (O) component may be 1 to 10 wt %, specifically 2 to 8 wt %. And the amount of other impurities (for example, —COOH, —OH, $O_2$, etc.) may be 0.001 to 0.1 wt %, specifically 0.001 to 0.05 wt %.

Figure 4:
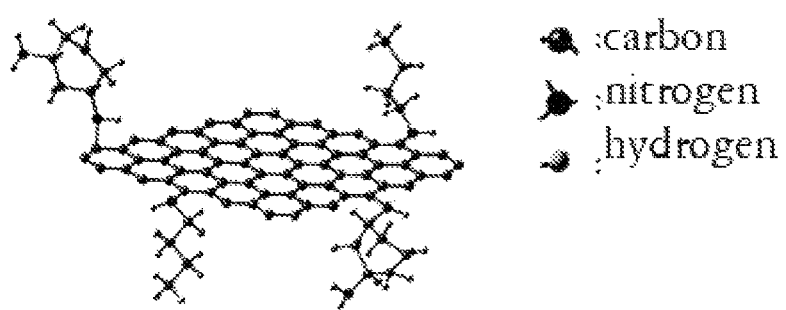
FIG. 4 and FIG. 5 show the structural formulas of functionalized graphenes in accordance with embodiments of the present invention.
Figure 5:
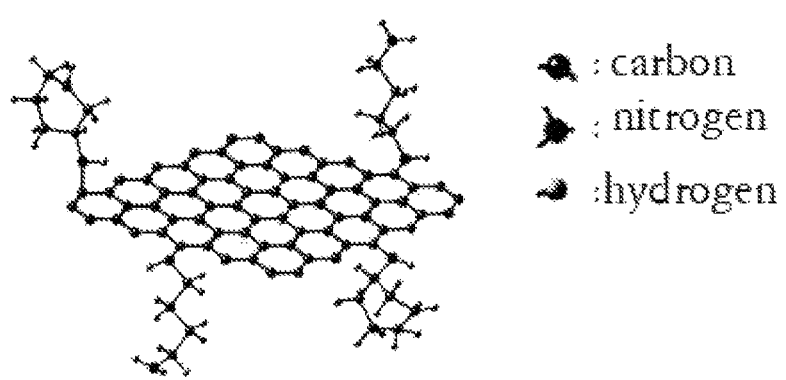

The functionalized graphene according to the present invention may have a structure represented by the structural formula 2 shown in FIG. 4 or structural formula 3 shown in FIG. 5.

As shown in the structural formula 2, the functionalized graphene has a structure of a butylamine group (n-butylamine, monovalent amine group) and a 3-aminohexylamine group (cyclohexanediamine, bivalent amine group) being chemically bonded to the carbon material.

As shown in the structural formula 3, the functionalized graphene has a structure of a cyclohexylamine group (a monovalent amine group) and a 4-aminobutylamine group (butyldiamine, bivalent amine group) being chemically bonded to the carbon material.

In order to produce a functionalized graphene according to the present invention, an amine solution (amine function-alized solution) is first prepared. The amine solution comprises a first amine compound, a second amine compound and a solvent. The first amine compound includes a monovalent amine, specifically a monovalent amine having 1 to 40 carbon atoms, more specifically 2 to 25 carbon atoms, most specifically 3 to 18 carbon atoms. The second amine compound includes a bivalent or higher amine, specifically a bivalent or higher amine having 1 to 40 carbon atoms, more specifically 2 to 25 carbon atoms, and most specifically 3 to 15 carbon atoms. The amount of the first and second amine compounds is 0.01 to 5 wt %, specifically 0.1 to 3 wt %, with respect to the total amount of the amine solution, and the ratio of the first and second amine compounds is 1:9 to 9:1. If the amount of the first and second amine compounds is out of the above range, the production efficiency of the amine solution may be lowered.

The solvent serves to dissolve the first and second amine compounds, and may be one or more selected from the group consisting of ethanol, isopropyl alcohol, methanol, distilled water, n-butanol, and mixtures thereof. The amount of the solvent to be used is not particularly limited and may be set as needed, for example, may be 95 to 99.99 wt %, specifically 97 to 99.9 wt %, with respect to the whole amine solution. If the amount of the solvent used is too small, the first and second amine compounds may not be sufficiently dissolved. If the amount is too large, the production efficiency of the amine solution may be lowered.

Next, a carbon material and a solvent are mixed to prepare a carbon material dispersion, and carbon material is selected from the group consisting of graphene, reduced graphene, graphene oxide, and mixtures thereof. The amount of the carbon material is 0.1 to 30 wt %, specifically 1 to 20 wt %, with respect to the entire carbon material dispersion. If the amount of the carbon material is out of the above range, the graphene characteristics may not be imparted, or the carbon material may not be dissolved. The solvent serves to dissolve the carbon material, so that there is no limitation as long as the carbon material can be dissolved. For example, as the solvent, one or more solvents selected from the group consisting of distilled water, isopropyl alcohol, methanol, ethanol, and mixtures thereof, specifically, distilled water may be used. The amount of the solvent to be used is not particularly limited and may be set as needed, for example, may be 70 to 99.9 wt %, specifically 80 to 99 wt %, with respect to entire carbon material dispersion. If the amount of the solvent is too small, the carbon material may not be sufficiently dissolved, and if the amount is too large, the production efficiency of the mixed solution may be lowered.

Next, the amine solution is added to the carbon material dispersion and then the mixture is stirred for 12 to 36 hours, particularly 20 to 30 hours at a temperature of 70 to 120° C., specifically 80 to 110° C., more specifically 85 to 105° C. Thereafter, the solvent in the mixture and the amine compounds not being bonded to the carbon material are removed using a conventionally available method (for example, a method of using a vacuum filtration kit or the like), and drying (for example, freeze-drying at −80° C. for more than 10 hours) is performed to produce a functionalized graphene in which the amine group is (e.g., chemically) bonded to the carbon material. The amount of the amine solution added is 5 to 20 parts by weight, specifically 7 to 15 parts by weight, with respect to 100 parts by weight of the carbon material dispersion. If the added amount of the amine solution is out of the above range, the amine material may not be sufficiently bonded to the carbon material, and the amphiphilic property may not be good.

The functionalized graphene according to the present invention can control the degree of hydrophobicity and hydrophilicity desired by controlling the addition amount of the amine solution.

FIG. 1 is a drawing illustrating a preparation example (a) of a functionalized graphene according to the present invention and productions (b, c) using the same. As shown in FIG. 1, the functionalized graphene according to the present invention can be used in a graphene ink composition, a graphene dispersion including a functionalized graphene and a solvent, a graphene coating solution or a polymer composite and so on. Further, the functionalized graphene according to the present invention can be applied to fillers for electrostatic discharge (ESD), electromagnetic interference (EMI) shielding, heat radiation (heat conductive), and materials for second battery electrode through the above examples. The coating solution and the ink composition are similar in composition but can be distinguished according to their application and viscosity. For example, when the functionalized graphene is intended to be coated on a film or the like, it is manufactured in a form of the coating solution and when high viscosity is needed and the functionalized graphene is intended for printing, it is manufactured in a form of the ink composition.

The functionalized graphene can be extruded together with a thermoplastic polymer or mixed with a thermosetting resin to be used as a filler for a graphene composite, and for example, can be applied to materials for ESD protection, EMI shielding, or heat dissipation (thermal conductive).

When the graphene dispersion is prepared using the functionalized graphene, it may further include a solvent. In such a case the amount of the functionalized graphene is 0.01 to 30 wt %, and the amount of the solvent is 70 to 99.99 wt %. When the functionalized graphene and the solvent are included in the above ranges, the dispersion effect is more excellent. When the amount of the functionalized graphene is too small, the characteristics (conductivity and heat dissipation) of the graphene may not be realized, and when it is too large, the value of the viscosity and the thixotropic index (TI) may be high, so that the dispersibility and fluidity of the composition for carbon material dispersion may be low.

When the coating solution or the ink composition is prepared using the functionalized graphene, a binder and a solvent may be further added. In such a case, the amount of the functionalized graphene is 0.01 to 30 wt %, the amount of the binder is 0.01 to 10 wt %, the amount of the solvent is 60 to 99.98 wt %. When the above-mentioned components are in the above ranges, the dispersibility of graphene is excellent to make electrical conductivity and thermal conductivity superior. When the amount of the functionalized graphene and binder is too small, graphene properties may be difficult to be realized, and when it is too large, the dispersibility and fluidity may be low.

As the binder, conventional binders can be employed. For example, polyurethane binder, acrylic binder, polyester binder, epoxy binder, polyvinyl binder, ethylene vinylacetate binder, melamine binder and mixture thereof can be used.

The solvent serves to dissolve the carbon material and the dispersant for carbon material, and can be one or more solvents selected from the group consisting of alcohols such as methanol, ethanol, isopropyl alcohol and the like, ketones such as methyl ethyl ketone (MEK) and methyl isobutyl ketone (MIBK) and the like, pyrrolidines such as n-methyl pyrrolidone (NMP) and the like, esters such as ethyl acetate and the like, aromatic esters such as benzyl acetate and the like, linear and/or branched hydrocarbons such as dimethoxyethane and 1-chlorobutane and the like, glycol ethers (cellosolves) such as ethyl cellosolve acetate, butyl cellosolve acetate (BCA) and the like, water ($H_2O$) and mixtures thereof.

Further to improve coating conditions and the like, the coating solution or ink composition may further comprise 0.001 to 10 wt % of a dispersant. Examples of the dispersants include hydroxyl carboxylic acid esters, acrylate copolymers, modified polyethers and mixtures thereof and the like.

When the polymer complex composition is prepared using the functionalized graphene, thermoplastic resin or thermosetting resin may be contained. In such a case, the amount of the functionalized graphene is 0.5 to 70 wt %, specifically 0.5 to 75 wt %, and the amount of thermoplastic resin or thermosetting resin is 30 to 99.5 wt %, specifically 25 to 99.5 wt %. Within this range, the dispersibility is excellent and the electrical characteristics and the thermal conductivity are more excellent. If the graphene amount is too low, the characteristics (conductivity and heat dissipation) of the graphene cannot be realized. If the graphene amount is too high, the viscosity or the melt flow index (MFI) is high so that the dispersibility and the fluidity of the composition become poor, which is not economical.

As the thermoplastic resin, a commonly used resin may be used, and for example polypropylene (PP), polyethylene (PE), ABS (acrylonitrile-butadiene-styerene resin), polyoxymethylene (POM), polycarbonate (PC), polybutylene terephthalate (PBT), polyphenylene sulfide (PPS), polyetherimide (PEI), polyetheretherketone (PEEK), liquid crystal polymer (LCP), nylon, PA6, thermoplastic elastomer (TPE) and so on can be used. As the thermosetting resin, a commonly used resin can be used. For example, an epoxy resin, a phenol resin, a urea resin and the like can be used.

The polymer composite may further include a lubricant and/or a dispersant for controlling the fluidity of the thermosetting resin and the resin during the extrusion process. For example, when a thermosetting resin is used as the resin, the dispersant may be further included, and when a thermoplastic resin is used, the lubricant may be further included. The amount of the lubricant and/or the dispersant is respectively 0.01 to 5 wt %. Examples of the lubricant include ester based wax, acid polyester based, stearic amide based, silicone-acryl based, siloxane based and mixtures thereof, and the like, and the examples of the dispersant include hydroxyl carboxylic acid ester, acrylate copolymer, modified polyether and mixtures thereof and the like.

EXAMPLES

Hereinafter, the present invention will be described in more detail with reference to Examples, but the present invention is not limited by the following Examples.

Manufacturing Example 1

Manufacturing of Reduced Graphene 0.5 wt % of graphene oxide (GO) and 99.5 wt % of distilled water were mixed, and thereto 1 part by weight of ascorbic acid (from Alfa Assar) was added. Thereafter, the temperature of the reactor was raised to 90° C. and centrifugation was performed (reduced) for 10 hours. Next, the residue was removed using a vacuum filtration kit, and washing with methanol was repeated five times to prepare the reduced graphene (rGO).

Example 1

Manufacturing of Functionalized Graphene 1 wt % of reduced graphene prepared in Manufacturing Example 1 and 99 wt % of distilled water were mixed to prepare a carbon material dispersion. 0.05 w % of n-butylamine, 0.05 wt % of cyclohexyldiamine and 99.9 wt % of methanol were uniformly mixed at room temperature to prepare an amine solution. To the carbon material dispersion was added 10 parts by weight of the amine solution, based on 100 parts by weight of the carbon material dispersion. The mixture solution in which the carbon material dispersion and the amine solution are mixed was stirred at 80° C. for 24 hours. Thereafter, the mixture solution was subjected to a vacuum filtration kit to remove the solvent and the residual amine compound, and then washed 5 times with a solvent mixed with methanol and distilled water at a weight ratio of 8:2, and dried in a vacuum oven to prepare functionalized graphene.

Example 2

Manufacturing of Functionalized Graphene

Functionalized graphene was prepared in the same manner as in Example 1 except that in the amine solution 0.025 wt % of n-butylamine and 0.075 wt % of cyclohexyldiamine were used instead of 0.05 wt % of n-butylamine and 0.05 wt % of cyclohexyldiamine.

Example 3

Manufacturing of Functionalized Graphene

Functionalized graphene was prepared in the same manner as in Example 1 except that in the amine solution 0.075 wt % of n-butylamine and 0.025 wt % of cyclohexyldiamine were used instead of 0.05 wt % of n-butylamine and 0.05 wt % of cyclohexyldiamine.

Example 4

Manufacturing of Functionalized Graphene

Functionalized graphene was prepared in the same manner as in Example 1 except that in the amine solution 0.05 wt % of cyclohexylamine and 0.05 wt % of cyclohexyldiamine were used instead of 0.05 wt % of n-butylamine and 0.05 wt % of cyclohexyldiamine.

Example 5

Manufacturing of Functionalized Graphene

Functionalized graphene was prepared in the same manner as in Example 1 except that in the amine solution 0.025 wt % of cyclohexylamine and 0.075 wt % of cyclohexyldiamine were used instead of 0.05 wt % of n-butylamine and 0.05 wt % of cyclohexyldiamine.

Example 6

Manufacturing of Functionalized Graphene

Functionalized graphene was prepared in the same manner as in Example 1 except that in the amine solution 0.075 wt % of cyclohexylamine and 0.025 wt % of cyclohexyldiamine were used instead of 0.05 wt % of n-butylamine and 0.05 wt % of cyclohexyldiamine.

Example 7

Manufacturing of Functionalized Graphene

Functionalized graphene was prepared in the same manner as in Example 1 except that in the amine solution 0.05 wt % of cyclohexylamine and 0.05 wt % of diaminobutane were used instead of 0.05 wt % of n-butylamine and 0.05 wt % of cyclohexyldiamine.

Example 8

Manufacturing of Functionalized Graphene

Functionalized graphene was prepared in the same manner as in Example 1 except that in the amine solution 0.025 wt % of cyclohexylamine and 0.075 wt % of diaminobutane were used instead of 0.05 wt % of n-butylamine and 0.05 wt % of cyclohexyldiamine.

Example 9

Manufacturing of Functionalized Graphene

Functionalized graphene was prepared in the same manner as in Example 1 except that in the amine solution 0.075 wt % of cyclohexylamine and 0.025 wt % of diaminobutane were used instead of 0.05 wt % of n-butylamine and 0.05 wt % of cyclohexyldiamine.

Example 10

Manufacturing of Functionalized Graphene

Functionalized graphene was prepared in the same manner as in Example 1 except that in the amine solution 0.05 wt % of n-butylamine and 0.05 wt % of diaminobutane were used instead of 0.05 wt % of n-butylamine and 0.05 wt % of cyclohexyldiamine.

Example 11

Manufacturing of Functionalized Graphene

Functionalized graphene was prepared in the same manner as in Example 1 except that in the amine solution 0.025 wt % of n-butylamine and 0.075 wt % of diaminobutane were used instead of 0.05 wt % of n-butylamine and 0.05 wt % of cyclohexyldiamine.

Example 12

Manufacturing of Functionalized Graphene

Functionalized graphene was prepared in the same manner as in Example 1 except that in the amine solution 0.075 wt % of n-butylamine and 0.025 wt % of diaminobutane were used instead of 0.05 wt % of n-butylamine and 0.05 wt % of cyclohexyldiamine.

Example 13

Manufacturing of Functionalized Graphene

Functionalized graphene was prepared in the same manner as in Example 1 except that in the amine solution 0.05 wt % of n-butylamine and 0.05 wt % of 1,4-phenyldiamine were used instead of 0.05 wt % of n-butylamine and 0.05 wt % of cyclohexyldiamine.

Example 14

Manufacturing of Functionalized Graphene

Functionalized graphene was prepared in the same manner as in Example 1 except that in the amine solution 0.05 wt % of n-butylamine and 0.05 wt % of 3,4-dimethylbenzene-1,2-diamine were used instead of 0.05 wt % of n-butylamine and 0.05 wt % of cyclohexyldiamine.

Example 15

Manufacturing of Functionalized Graphene

Functionalized graphene was prepared in the same manner as in Example 1 except that in the amine solution 0.05 wt % of n-butylamine and 0.05 wt % of 1,3-cyclohexanebis(methylamine) were used instead of 0.05 wt % of n-butylamine and 0.05 wt % of cyclohexyldiamine.

Comparative Example 1

Manufacturing of Functionalized Graphene 2 wt % of reduced graphene prepared in Manufacturing Example 1 and 98 wt % of distilled water were mixed to prepare a carbon material dispersion. The carbon material dispersion was stirred at 80° C. for 24 hours. Thereafter, the carbon material dispersion was subjected to a vacuum filtration kit to remove the solvent, and then washed 5 times with a solvent mixed with methanol and distilled water at a weight ratio of 8:2, and dried in a vacuum oven to prepare functionalized graphene.

Comparative Example 2

Manufacturing of Functionalized Graphene 2 wt % of reduced graphene prepared in Manufacturing Example 1 and 98 wt % of distilled water were mixed to prepare a carbon material dispersion. 0.1 w % of n-butylamine and 99.9 wt % of methanol were uniformly mixed at room temperature to prepare an amine solution. To the carbon material dispersion was added 10 parts by weight of the amine solution, based on 100 parts by weight of the carbon material dispersion. The mixture solution are mixed was stirred at 80° C. for 24 hours. Thereafter the mixture solution was subjected to a vacuum filtration kit to remove the solvent and the residual amine compound, washed 5 times with a solvent mixed with methanol and distilled water at a weight ratio of 8:2, and dried in a vacuum oven to prepare functionalized graphene.

Comparative Example 3

Manufacturing of Functionalized Graphene

Functionalized graphene was prepared in the same manner as in Comparative Example 2 except that cyclohexylamine was used instead of n-butylamine.

Comparative Example 4

Manufacturing of Functionalized Graphene

Functionalized graphene was prepared in the same manner as in Comparative Example 2 except that octadecylamine was used instead of n-butylamine.

Comparative Example 5

Manufacturing of Functionalized Graphene

Functionalized graphene was prepared in the same manner as in Comparative Example 2 except that diaminobutane was used instead of n-butylamine.

Comparative Example 6

Manufacturing of Functionalized Graphene

Functionalized graphene was prepared in the same manner as in Comparative Example 2 except that cyclohexyldiamine was used instead of n-butylamine.

Comparative Example 7

Manufacturing of Functionalized Graphene

Functionalized graphene was prepared in the same manner as in Comparative Example 2 except that octadecyldiamine was used instead of n-butylamine.

Comparative Example 8

Manufacturing of Functionalized Graphene

Functionalized graphene was prepared in the same manner as in Comparative Example 2 except that 1,4-phenyldiamine was used instead of n-butylamine.

Comparative Example 9

Manufacturing of Functionalized Graphene

Functionalized graphene was prepared in the same manner as in Comparative Example 2 except that 3,4-dimethylbenzene-1,2-diamine was used instead of n-butylamine.

Comparative Example 10

Manufacturing of Functionalized Graphene

Functionalized graphene was prepared in the same manner as in Comparative Example 2 except that 1,3-cyclohexanebis(methylamine) was used instead of n-butylamine.

Comparative Example 11

Manufacturing of Functionalized Graphene

Functionalized graphene was prepared in the same manner as in Comparative Example 2 except that 0.05 wt % of n-butylamine and 0.05 wt % of cyclohexylamine was used instead of n-butylamine.

Comparative Example 12

Manufacturing of Functionalized Graphene

Functionalized graphene was prepared in the same manner as in Comparative Example 2 except that 0.05 wt % of diaminobutane and 0.05 wt % of cyclohexyldiamine was used instead of n-butylamine.

Experimental Example 1

Evaluation of Electrical Characteristics of Functionalized Graphene 0.5 wt % the functionalized graphene prepared in each of Examples 1 to 15 and Comparative Examples 1 to 12, 94.5 wt % of methanol and 5 wt % of a polyester resin (COO Chemical Co., Ltd) were mixed and stirred for 30 minutes to produce mixture solution. Ceramic beads were added to the prepared mixed solution and dispersed with a shaker (DAS 200) to prepare a dispersion. The dispersion was coated on a polyethylene terephthalate (PET) film using automatic film applicator. Then the film was placed in a hot-air oven set at a temperature of 100° C. for 3 minutes for drying, and the sheet resistivity of the dried film was measured using a 4-point probe. The results are shown in Table 1 below.

TABLE 1

| | Amine compound (functionalized compound) | Sheet resistivity ($\Omega$/sq) |
| --- | --- | --- |
| Example 1 | Adding of n-butylamine (0.05 wt %) + cyclohexyldiamine (0.05 wt %) | $10^{5.7}$ |
| Example 2 | Adding of n-butylamine (0.025 wt %) + cyclohexyldiamine (0.075 wt %) | $10^{5.8}$ |
| Example 3 | Adding of n-butylamine (0.075 wt %) + cyclohexyldiamine (0.025 wt %) | $10^{5.9}$ |
| Example 4 | Adding of cyclohexylamine (0.05 wt %) + cyclohexyldiamine (0.05 wt %) | $10^{5.8}$ |
| Example 5 | Adding of cyclohexylamine (0.025 wt %) + cyclohexyldiamine (0.075 wt %) | $10^{6.0}$ |
| Example 6 | Adding of cyclohexylamine (0.075 wt %) + cyclohexyldiamine (0.025 wt %) | $10^{6.1}$ |
| Example 7 | Adding of cyclohexylamine (0.05 wt %) + diaminobutane (0.05 wt %) | $10^{6.0}$ |
| Example 8 | Adding of cyclohexylamine (0.025 wt %) + diaminobutane (0.075 wt %) | $10^{6.1}$ |
| Example 9 | Adding of cyclohexylamine (0.075 wt %) + diaminobutane (0.025 wt %) | $10^{6.2}$ |
| Example 10 | Adding of n-butylamine (0.05 wt %) + diaminobutane (0.05 wt %) | $10^{6.2}$ |
| Example 11 | Adding of n-butylamine (0.025 wt %) + diaminobutane (0.075 wt %) | $10^{6.3}$ |
| Example 12 | Adding of n-butylamine (0.075 wt %) + diaminobutane (0.025 wt %) | $10^{6.4}$ |
| Example 13 | n-butylamine (0.05 wt %) + 1,4-phenyldiamine (0.05 wt %) | $10^{6.8}$ |
| Example 14 | n-butylamine (0.05 wt %) + 3,4-dimethyl-benzen-1,2 diamine (0.05 wt %) | $10^{7.1}$ |
| Example 15 | n-butylamine (0.05 wt %) + 1,3-cyclohexanebis(methylamine)(0.05 wt %) | $10^{5.8}$ |
| Comparative Example 1 | Dispersed without adding functional agents | $10^{8.5}$ |
| Comparative Example 2 | Adding of n-butylamine (0.1 wt %) | $10^{6.2}$ |
| Comparative Example 3 | Adding of cyclohexylamine (0.1 wt %) | $10^{5.8}$ |
| Comparative Example 4 | Adding of octadecylamine (0.1 wt %) | $10^{6.7}$ |
| Comparative Example 5 | Adding of diaminobutane (0.1 wt %) | $10^{6.5}$ |
| Comparative Example 6 | Adding of cyclohexyldiamine(0.1 wt %) | $10^{5.9}$ |
| Comparative Example 7 | Adding of octadecyldiamine (0.1 wt %) | $10^{6.9}$ |
| Comparative Example 8 | Adding of 1,4-phenyldiamine (0.1 wt %) | $10^{8.4}$ |
| Comparative Example 9 | Adding of 3,4-dimethyl-benzen-1,2 diamine (0.1 wt %) | $10^{8.7}$ |
| Comparative Example 10 | 1,3-cyclohexanebis(methylamine)(0.05 wt %) | $10^{5.9}$ |
| Comparative Example 11 | Adding of n-butylamine (0.05 wt %) + cyclohexylamine (0.05 wt %) | $10^{6.6}$ |
| Comparative Example 12 | Adding of diaminobutane (0.05 wt %) + cyclohexyldiamine(0.05 wt %) | $10^{6.7}$ |

As shown from the above Table 1, the sheet resistivity of the functionalized graphene prepared by adding the amine compound was measured to be lower than that of the graphene without the amine compound. Even when the amine compound was added, the sheet resistivity was measured to be lower when the monovalent amine and the bivalent amine were simultaneously included. Specifically, when a monovalent linear amine and a bivalent cyclic amine group (for example, a cyclic amine group) are included at the same time (in Example 1 (0.05 wt % of n-butylamine and 0.05 wt % of cyclohexyldiamine)), the sheet resistivity was the lowest.

Experimental Example 2

Confirmation of Functionalization of Graphene

The functionalized graphenes prepared in Examples 1 to 3 and Comparative Examples 1, 2 and 6 were analyzed by XPS (X-ray photoelectron spectroscopy, VG Microtech ESCA2000), and the results thereof are shown in Table 2 below in which N1S peaks were observed, thereby confirming functionalization of the functionalized graphene. Here, by using C1S, O1S and N1S, the respective structures in the functionalized graphene and the kind of the bond can be known. In such a case, the N1S peak may be obtained even when the amine is not included (in the case of Comparative Example 1, etc.) due to influence from the atmosphere or the external environment at the time of measurement. When N1IS is 0.001 to 0.1%, it can be considered that graphene is not functionalized.

TABLE 2

| | Amine solution | C1S | O1S | N1S |
|---|---|---|---|---|
| Example 1 | n-butylamine (0.05 wt %) + cyclohexyldiamine(0.05 wt %) | 90.67 | 8.75 | 0.58 |

TABLE 2-continued

| | Amine solution | C1S | O1S | N1S |
|---|---|---|---|---|
| Example 2 | n-butylamine (0.025 wt %) + cyclohexyldiamine(0.075 wt %) | 90.88 | 8.39 | 0.73 |
| Example 3 | n-butylamine (0.075 wt %) + cyclohexyldiamine (0.025 wt %) | 90.2 | 9.37 | 0.43 |
| Comparative Example 1 | Dispersed without adding functional agents | 89.25 | 10.749 | 0.001 |
| Comparative Example 2 | n-butylamine (0.1 wt %) | 89.75 | 9.37 | 0.88 |
| Comparative Example 6 | cyclohexyldiamine(0.1 wt %) | 87.245 | 12.476 | 0.279 |

Experimental Example 3

Evaluation of Dispersibility of Functionalized Graphene 99.5 wt % of distilled water, alcohol and solvents (dimethyl sulfoxide (DMSO), n-methyl-pyrrolidone (NMP), propylene glycol monomethyl ether acetate (PGMEA), cyclohexene)) respectively was added to 0.5 wt % of the functionalized graphene prepared in Examples 1 to 15 and Comparative Examples 1 to 12, and was stirred for 30 minutes to prepare mixture solutions. Ceramic beads were mixed with the prepared mixture solutions each and dispersed for 80 minutes using a shaker (DAS 200) to prepare dispersions. The dispersion was poured into each vial in 10 ml, and it was checked whether or not the powder was settled at elapsed time of 1 hour, 24 hours, and 168 hours. The results are shown in Tables 3 and 4 below in which the degree of sedimentation is represented by symbols of ⊚, ○, Δ and X, which shows becoming large in order of the right direction.

TABLE 3

| | Elapsed days (Elapsed time) | Distilled water | DMSO | NMP | MeOH | PGMEA | Cyclohexene |
|---|---|---|---|---|---|---|---|
| Example 1 | Day 0 (1 h) | ○ | ○ | ○ | ○ | ○ | ○ |
| | Day 1 (24 h) | ○ | ○ | ○ | ○ | ○ | ○ |
| | Day 7 (168 h) | Δ | ○ | ○ | ○ | ○ | ○ |
| Example 2 | Day 0 (1 h) | ○ | ○ | ○ | ○ | ○ | ○ |
| | Day 1 (24 h) | ○ | ○ | ○ | ○ | ○ | ○ |
| | Day 7 (168 h) | ○ | ○ | ○ | ○ | Δ | Δ |
| Example 3 | Day 0 (1 h) | ○ | ○ | ○ | ○ | ○ | ○ |
| | Day 1 (24 h) | ○ | ○ | ○ | ○ | ○ | ○ |
| | Day 7 (168 h) | Δ | ○ | ○ | Δ | ○ | ○ |
| Example 4 | Day 0 (1 h) | ○ | ○ | ○ | ○ | Δ | ○ |
| | Day 1 (24 h) | Δ | Δ | Δ | Δ | Δ | ○ |
| | Day 7 (168 h) | Δ | Δ | Δ | Δ | Δ | ○ |
| Example 5 | Day 0 (1 h) | ○ | ○ | ○ | ○ | Δ | ○ |
| | Day 1 (24 h) | Δ | Δ | Δ | ○ | Δ | ○ |
| | Day 7 (168 h) | Δ | Δ | Δ | Δ | Δ | ○ |
| Example 6 | Day 0 (1 h) | ○ | ○ | ○ | ○ | ○ | ○ |
| | Day 1 (24 h) | Δ | Δ | Δ | ○ | Δ | ○ |
| | Day 7 (168 h) | Δ | Δ | Δ | Δ | Δ | ○ |
| Example 7 | Day 0 (1 h) | Δ | ○ | ○ | ○ | ○ | ○ |
| | Day 1 (24 h) | Δ | ○ | ○ | Δ | ○ | ○ |
| | Day 7 (168 h) | Δ | Δ | Δ | Δ | Δ | ○ |
| Example 8 | Day 0 (1 h) | ○ | ○ | ○ | Δ | Δ | ○ |
| | Day 1 (24 h) | Δ | ○ | ○ | Δ | Δ | Δ |
| | Day 7 (168 h) | Δ | Δ | Δ | Δ | X | X |
| Example 9 | Day 0 (1 h) | ○ | ○ | ○ | ○ | Δ | ○ |
| | Day 1 (24 h) | Δ | ○ | ○ | ○ | Δ | ○ |
| | Day 7 (168 h) | Δ | Δ | Δ | Δ | Δ | ○ |
| Example 10 | Day 0 (1 h) | ○ | ○ | ○ | ○ | Δ | ○ |
| | Day 1 (24 h) | Δ | ○ | ○ | ○ | Δ | ○ |
| | Day 7 (168 h) | Δ | Δ | Δ | Δ | Δ | ○ |

TABLE 3-continued

|  | Elapsed days (Elapsed time) | Distilled water | DMSO | NMP | MeOH | PGMEA | Cyclohexene |
|---|---|---|---|---|---|---|---|
| Example 11 | Day 0 (1 h) | ○ | ○ | ○ | ○ | Δ | ○ |
|  | Day 1 (24 h) | Δ | Δ | Δ | Δ | Δ | ○ |
|  | Day 7 (168 h) | Δ | Δ | Δ | Δ | Δ | ○ |
| Example 12 | Day 0 (1 h) | Δ | ○ | Δ | ○ | ○ | ○ |
|  | Day 1 (24 h) | Δ | Δ | Δ | Δ | ○ | ○ |
|  | Day 7 (168 h) | Δ | Δ | Δ | Δ | Δ | Δ |

TABLE 4

|  | Elapsed days (Elapsed time) | Distilled Water | DMSO | NMP | MeOH | PGMEA | Cyclohexene |
|---|---|---|---|---|---|---|---|
| Example 13 | Day 0 (1 h) | ○ | ○ | ○ | ○ | ○ | ○ |
|  | Day 1 (24 h) | Δ | Δ | Δ | Δ | ○ | Δ |
|  | Day 7 (168 h) | X | X | X | X | Δ | Δ |
| Example 14 | Day 0 (1 h) | Δ | Δ | Δ | Δ | ○ | ○ |
|  | Day 1 (24 h) | X | X | X | Δ | ○ | ○ |
|  | Day 7 (168 h) | X | X | X | Δ | Δ | Δ |
| Example 15 | Day 0 (1 h) | ○ | ○ | ○ | ○ | ○ | ○ |
|  | Day 1 (24 h) | ○ | ○ | Δ | ○ | ○ | ○ |
|  | Day 7 (168 h) | Δ | Δ | Δ | ○ | ○ | ○ |
| Comparative Example 1 | Day 0 (1 h) | X | X | X | Δ | ○ | ○ |
|  | Day 1 (24 h) | X | X | X | X | Δ | Δ |
|  | Day 7 (168 h) | X | X | X | X | X | X |
| Comparative Example 2 | Day 0 (1 h) | ○ | ⊚ | ○ | ○ | X | X |
|  | Day 1 (24 h) | ○ | ⊚ | ○ | Δ | X | X |
|  | Day 7 (168 h) | ○ | ⊚ | ○ | X | X | X |
| Comparative Example 3 | Day 0 (1 h) | ○ | ○ | ○ | X | Δ | ○ |
|  | Day 1 (24 h) | Δ | ○ | Δ | X | Δ | ○ |
|  | Day 7 (168 h) | Δ | Δ | Δ | X | X | Δ |
| Comparative Example 4 | Day 0 (1 h) | Δ | Δ | Δ | Δ | ○ | ○ |
|  | Day 1 (24 h) | X | X | X | X | ○ | ○ |
|  | Day 7 (168 h) | X | X | X | X | ○ | Δ |
| Comparative Example 5 | Day 0 (1 h) | ○ | ○ | ○ | ○ | Δ | Δ |
|  | Day 1 (24 h) | Δ | ○ | ○ | ○ | Δ | Δ |
|  | Day 7 (168 h) | X | Δ | Δ | ○ | Δ | Δ |
| Comparative Example 6 | Day 0 (1 h) | Δ | ○ | ○ | ○ | Δ | Δ |
|  | Day 1 (24 h) | Δ | ○ | ○ | ○ | Δ | Δ |
|  | Day 7 (168 h) | X | ○ | ○ | ○ | Δ | Δ |
| Comparative Example 7 | Day 0 (1 h) | Δ | Δ | Δ | Δ | ○ | ○ |
|  | Day 1 (24 h) | Δ | Δ | Δ | Δ | ○ | Δ |
|  | Day 7 (168 h) | X | X | X | X | Δ | Δ |
| Comparative Example 8 | Day 0 (1 h) | Δ | Δ | Δ | Δ | ○ | ○ |
|  | Day 1 (24 h) | Δ | Δ | Δ | Δ | ○ | Δ |
|  | Day 7 (168 h) | X | X | X | X | Δ | Δ |
| Comparative Example 9 | Day 0 (1 h) | Δ | Δ | Δ | Δ | ○ | ○ |
|  | Day 1 (24 h) | X | X | X | X | ○ | Δ |
|  | Day 7 (168 h) | X | X | X | X | Δ | Δ |
| Comparative Example 10 | Day 0 (1 h) | Δ | ○ | ○ | ○ | Δ | Δ |
|  | Day 1 (24 h) | Δ | Δ | ○ | ○ | Δ | Δ |
|  | Day 7 (168 h) | Δ | Δ | ○ | ○ | Δ | Δ |

As can be seen from Tables 3 and 4, it can be seen that the dispersibility in various solvents is excellent when the monovalent amine group and bivalent amine group are simultaneously used (Examples 1 to 15), compared to the functionalized graphene which independently contain or not contain monovalent or bivalent amine groups (Comparative Examples 1 to 10). In particular, even when two monovalent amine groups or two bivalent amine groups are contained (Comparative Examples 11 and 12), functionalized graphene (Examples 1 and 2) comprising a monovalent amine group having a relatively small number of carbon atoms and a bivalent amine group having a cyclic structure having a relatively large number of carbon atoms has most excellent uniformity of dispersion and the dispersion stability.

Experimental Example 4

Evaluation of Functionalized Graphene-Thermoplastic Resin Composite 3 wt % of each of the functionalized graphene prepared in Example 1 and the non-functionalized graphene prepared in Examples 1 and Comparative Examples 1 to 3 and 97 wt % of polybutylene terephthalate (manufactured by Samyang Corporation) were mixed for 20 minutes in a blending shaker, and the mixture was extruded using a twin-screw extruder (manufactured by Bautek, Ba19) and made into pellets by using a pelletizer (cutting the line-shaped composite into pellet form). The pellets prepared were melted at 260° C. by using a hot press and were manufactured as a test specimen in a mold of 60×60 mm×1.5T, whose electrical property was measured using a 4-point probe and thermal conductivity was measured using a thermal conductivity meter (TPS500S, HOT DISK). The results are shown in Table 5 below.

TABLE 5

| | Sheet resistivity (Ω/sq) | Thermal conductivity (W/mK) |
|---|---|---|
| Comparative Example 1 | $10^{13}$ | 1.0 |
| Comparative Example 2 | $10^{10}$ | 1.1 |
| Comparative Example 3 | $10^{8.5}$ | 1.4 |
| Example 1 | $10^{8}$ | 1.5 |

As shown in Table 5, it can be seen that the dispersion uniformity in the thermoplastic resin is excellent and the electrical characteristics and the thermal conductivity are excellent when the monovalent and bivalent amine groups are simultaneously applied (Example 1), compared to the functionalized graphene which independently contain or not contain monovalent or bivalent amine groups (Comparative Examples 1 to 3).

The invention claimed is:

1. A functionalized graphene with an amine group comprising:
    a carbon material selected from a group consisting of graphene, reduced graphene, graphene oxide, and mixture thereof; and
    a monovalent amine group and a bivalent or higher amine group which are bonded to the carbon material,
    wherein a molar ratio of the monovalent amine group and the bivalent or higher amine group is 1:9 to 9:1.

2. The functionalized graphene according to claim 1, wherein the amount of the carbon material is 85 to 99.9 wt % and the amount of amine group is 0.1 to 15 wt %.

3. The functionalized graphene according to claim 1, wherein the monovalent amine group and the bivalent or higher amine group are bonded to different position of the carbon material.

4. The functionalized graphene according to claim 1, wherein the monovalent amine group is monovalent amine having 1 to 40 carbon atoms and the bivalent or higher amine group is bivalent or higher amine having 1 to 40 carbon atoms.

5. The functionalized graphene according to claim 1, wherein the monovalent amine group is selected from the group consisting of n-butylamine, cyclohexylamine, n-hexylamine, phenylpropylamine, phenylbutylamine, octadecylamine, dodecylamine and mixtures thereof, and the bivalent or higher amine group is selected from the group consisting of n-diaminocyclohexane, n-diaminobutane, n-hexyldiamine, p-phenyldiamine, ethylenediamine, diaminododecane, 3,4-dimethyl-benzene-1,2-diamine, and mixtures thereof.

6. The functionalized graphene according to claim 1, wherein the monovalent amine group is chain alkylamine group having 3 to 18 carbon atoms and the bivalent or higher amine group is cyclic alkylamine group having 6 to 15 carbon atoms.

7. A method for preparing a functionalized graphene comprising the steps of:
    mixing a carbon material and a first solvent to prepare a carbon material dispersion, the carbon material being selected from a group consisting of graphene, reduced graphene, graphene oxide and mixture thereof; and
    adding to the carbon material dispersion an amine solution in which a first amine compound having a monovalent amine group, a second amine compound having a bivalent or higher amine group and a second solvent are mixed, to chemically bond the amine group to the carbon material,
    wherein a molar ratio of the monovalent amine group and the bivalent or higher amine group is 1:9 to 9:1.

8. The method according to claim 7, wherein in the carbon material dispersion the amount of the carbon material is 0.1 to 30 wt % and the amount of the first solvent is 70 to 99.9 wt %, and in the amine solution the first amine compound is an amine compound having 1 to 40 carbon atoms, the second amine compound is an amine compound having 1 to 40 carbon atoms, the amount of the first and second amine compounds is 0.01 to 5 wt % with respect to the total amount of the amine solution, and the ratio of the first and second amine compounds is 1: 9 to 9: 1, and the amount of the second solvent is 95 to 99.9 wt %, and the amount of the amine solution added is of 5 to 20 parts by weight with respect to 100 parts by weight of the carbon material dispersion.

9. The method according to claim 7, wherein the hydrophobicity and hydrophilicity of the functionalized graphene are controlled by controlling amount of the amine group.

10. A graphene composition comprising functionalized graphene according to claim 1.

11. The graphene composition according to claim 10, further comprising solvent.

12. The graphene composition according to claim 11, further comprising binder.

13. A graphene composite comprising functionalized graphene according to claim 1.

14. The graphene composite according to claim 13, further comprising thermoplastic resin or thermosetting resin.

15. A functionalized graphene with an amine group comprising:
    a carbon material selected from a group consisting of graphene, reduced graphene, graphene oxide, and mixture thereof; and
    a monovalent amine group and a bivalent or higher amine group which are bonded to the carbon material,
    wherein the bivalent or higher amine group is cyclic alkylamine group having 6 to 15 carbon atoms.

* * * * *